United States Patent [19]

Rosenberger

[11] Patent Number: 4,513,109

[45] Date of Patent: Apr. 23, 1985

[54] PHENOLS AND USE THEREOF AS STABILIZERS

[75] Inventor: Siegfried Rosenberger, Riehen, Switzerland

[73] Assignee: Ciba-Geigy Corporation, Ardsley, N.Y.

[21] Appl. No.: 574,422

[22] Filed: Jan. 27, 1984

Related U.S. Application Data

[63] Continuation of Ser. No. 520,374, Aug. 4, 1983, abandoned, which is a continuation of Ser. No. 445,889, Dec. 1, 1982, abandoned.

[30] Foreign Application Priority Data

Dec. 3, 1981 [CH] Switzerland ..................... 7734/81

[51] Int. Cl.$^3$ .................... C08K 5/13; C07C 39/12; C07C 39/17
[52] U.S. Cl. ................... 524/342; 252/52 R; 524/331; 524/339; 568/47; 568/640; 568/650; 568/652; 568/568; 568/720
[58] Field of Search ............. 524/339, 331, 342; 568/640, 650, 652, 47, 720; 252/52 R

[56] References Cited

U.S. PATENT DOCUMENTS

| | | | |
|---|---|---|---|
| 3,035,908 | 5/1962 | Gottshall | 568/47 |
| 3,234,290 | 2/1966 | Rocklin | 568/47 |
| 3,346,648 | 10/1967 | Worrel | 260/611 |
| 3,640,761 | 2/1972 | Hamanaka et al. | 427/214 |
| 3,704,326 | 11/1972 | Song | 568/47 |
| 3,795,700 | 3/1974 | Song et al. | 260/475 P |

FOREIGN PATENT DOCUMENTS

| | | |
|---|---|---|
| 3338 | 8/1979 | European Pat. Off. . |
| 48-14181 | of 1973 | Japan . |
| 1229574 | 4/1971 | United Kingdom . |
| 1349669 | 4/1974 | United Kingdom . |

OTHER PUBLICATIONS

Chem. Ber. 98 (10), 3264, (1965).
Scott, Gerald, "Atmospheric Oxidation and Antioxidants", (1965), 124 and 125, Elsevier Pub. Co., N.Y.

*Primary Examiner*—Veronica P. Hoke
*Attorney, Agent, or Firm*—Luther A. R. Hall

[57] ABSTRACT

The invention relates to phenols which contain a number of aromatic nuclei and in which the bridge formation of these nuclei is in the meta-position to the OH groups. These phenols have the formula I, wherein $R^1$, $R^2$, $R^3$ and $R^4$ are as defined in claim 1.

The novel phenols are most suitable for use as stabilizers for organic polymers and lubricants and have particularly good color properties.

5 Claims, No Drawings

PHENOLS AND USE THEREOF AS STABILIZERS

This is a continuation of application Ser. No. 520,374, filed Aug. 4, 1983, now abandoned, which in turn is a continuation of application Ser. No. 445,889, filed Dec. 1, 1982, now abandoned.

The present invention relates to novel meta-functional phenols, in particular to phenols which carry OH groups in at least two aromatic nuclei, which are useful stabilisers for organic material.

There are already known from the literature a number of phenols which carry OH groups in at least two aromatic nuclei and in which the aromatic nuclei are linked through bridge radicals, each nucleus carrying the OH group in ortho- or para-position to the carbon atom through which the linkage to the second aromatic nucleus occurs or where the OH substitution is nuclear. The use of such phenols as stabilisers is also known. Such phenols are described e.g. in the following publications: U.S. Pat. No. 3,346,648, German Offenlegungsschrift No. 2 138 839, and Japanese patent specification No. 7 314 181.

There are also known from the literature a few phenols which carry OH groups in at least two aromatic nuclei, said OH groups being in meta-position to the carbon atom through which the linkage to the second aromatic nucleus occurs. The use of such phenols as antioxidants is also known. Reference is made in this connection to German Offenlegungsschrift No. 2 211 722 and to a publication by H. Budzikiewicz and J. Swoboda in Chem. Ber. 98 (10), 1965, 3264-9.

The meta-functional phenols of this invention have better activity and colour properties as antioxidants than the known compounds cited above.

The present invention relates to compounds of the formula I

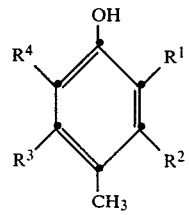

(I)

wherein $R^1$ is $C_1$–$C_4$alkyl, $R^4$ is $C_1$–$C_{12}$alkyl, $C_5$–$C_8$cycloalkyl, $C_6$–$C_{10}$aryl, $C_7$–$C_{10}$aralkyl or $C_7$–$C_{10}$alkaryl, and each of $R^2$ and $R^3$ independently of the other is one of the radicals of the formulae II, III or IV

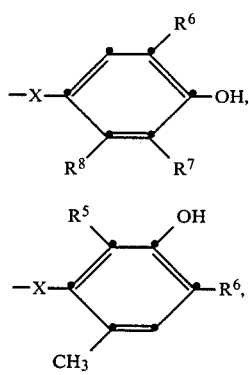

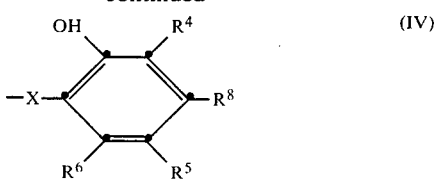

wherein $R^5$ and $R^6$ are as defined above for $R^1$ and $R^4$ and both radicals may be identical to or different from $R^1$ and $R^4$, and X is —$CH_2$—, —$CH_2OCH_2$— or —$CH_2SCH_2$—, $R^7$ is $C_4$–$C_{12}$-alkyl, $C_5$–$C_8$cycloalkyl, $C_6$–$C_{10}$aryl, $C_7$–$C_{10}$aralkyl or $C_7$–$C_{10}$alkaryl and $R^8$ is methyl or hydrogen.

$R^1$, $R^4$, $R^5$, $R^6$ and $R^7$ is $C_1$–$C_4$alkyl, $C_1$–$C_{12}$alkyl or $C_4$–$C_{12}$alkyl may be methyl, ethyl, n-propyl, isopropyl, n-butyl, sec-butyl, tert-butyl, n-pentyl, n-hexyl, n-octyl, 1,1,3,3-tetramethylbutyl, n-nonyl, decyl or dodecyl. $R^1$, $R^4$, $R^5$ and $R^6$ are each preferably methyl or tert-butyl. The preferred significance of $R^7$ is tert-butyl.

$R^4$, $R^6$ and $R^7$ as $C_6$–$C_{10}$aryl may be naphthyl and preferably phenyl.

$R^4$, $R^6$ and $R^7$ as $C_7$–$C_{10}$aralkyl may be benzyl, 1-phenylethyl, α,α-dimethylbenzyl or 2-phenylethyl.

$R^4$, $R^6$ and $R^7$ as $C_5$–$C_8$cycloalkyl may be cyclopentyl, cycloheptyl, cyclooctyl and preferably cyclohexyl.

$R^4$, $R^6$ and $R^7$ as $C_7$–$C_{10}$alkaryl may be tolyl, 2,4-dimethylphenyl, 2,6-dimethylphenyl, 2,4-diethylphenyl, 2,6-diethylphenyl or 4-tert-butylphenyl, with 2,4-dimethylphenyl being preferred.

Preferred compounds of the formula I are those in which each of $R^2$ and $R^3$ independently of the other is a radical of the formula II or IV, and especially those which contain $R^2$ and $R^3$ as radicals of the formula II.

Where $R^2$ and/or $R^3$ in formula I are radicals of the formula III, the substituents $R^5$ and $R^6$ are preferably $C_1$–$C_4$alkyl. The radicals $R^1$ and $R^4$ are then preferably methyl.

The preferred significance of X is —$CH_2$—.

Compounds of the formula I, wherein $R^1$ and $R^5$ are each methyl, each of $R^4$ and $R^6$ independently of the other is $C_1$–$C_4$alkyl, $R^7$ is tert-butyl, $R^8$ is hydrogen and each of $R^2$ and $R^3$ independently of the other is a radical of the formula II or III, constitute a preferred embodiment of the invention.

The following compounds are examples of the compounds of this invention:
of the formula I: 3,5-di-(3',5'-di-tert-butyl-4'-hydroxybenzyl)-2,4-dimethyl-6-tert-butylphenol, 3,5-di-(3',5'-di-tert-butyl-4'-hydroxybenzyl)-2,4,6-trimethylphenol, 3,5-di-(3'-methyl-5'-tert-butyl-6'-hydroxybenzyl)-2,4,6-trimethylphenol, 3,5-di-(2',6'-dimethyl-4'-tert-butyl-3'-hydroxybenzyl)-2,4,6-trimethylphenol, 3,5-di-(2',4'-di-tert-butyl-6'-methyl-3'-hydroxybenzyl)-2,4,6-trimethylphenol.

The polynuclear stabilisers of the formula I may be obtained by known benzylation reactions of hindered phenols, by reacting a phenol of the formula V

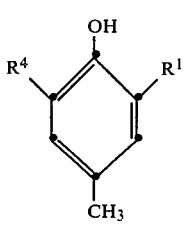

with at least one benzylating component of the formulae VI, VII and/or VIII

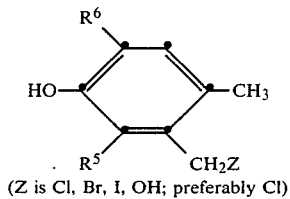

(Z is Cl, Br, I, OH; preferably Cl)

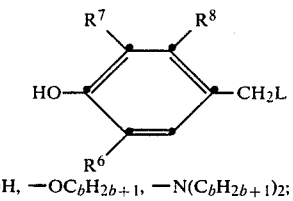

(L is OH, $-OC_bH_{2b+1}$, $-N(C_bH_{2b+1})_2$; b = 1–4.)

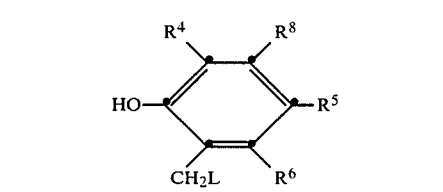

the molar ratio of the compound of the formula V to the sum of the compounds of the formulae VI, VII and VIII being approximately 1:2.

The reaction may be carried out in the presence of a base (e.g. a tertiary amine, an alkali metal or an alkaline earth metal), and also, if desired, in the presence of an acid catalyst such as $H_2SO_4$, HCl, p-toluene sulfonic acid, $BF_3$ etherate, $ZnCl_2$, $AlCl_3$, and in the presence of an inert solvent (e.g. an alkane, aromatic, ether, dimethylformamide, dimethylacetamide). An excess of the compounds of the formulae VI, VII and VIII may also be used in the reaction.

The starting materials employed for obtaining the compounds of this invention are known compounds, the preparation of which is likewise known to the skilled person.

The present invention also relates to the use of compounds of the formula I as stabilisers for protecting organic material against the action of oxygen, heat, light and ionising radiation, e.g. $\beta$- and $\gamma$-radiation.

Preferred embodiments of this utility are the use of the compounds of the formula I as stabilisers for organic polymers, especially for graft polymers based on acrylonitrile, butadiene, styrene (ABS) or impact-resistant polystyrene. Further examples of organic material which can be conveniently stabilised with the compounds of the invention are:

1. Polymers of mono- and diolefins, for example polyethylene (which may be crosslinked), polypropylene, polyisobutylene, polybut-1-ene, polymethylpent-1-ene, polyisoprene or polybutadiene, and polymers of cycloolefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (ionomers), and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene, or styrene-ethylene/propylene-styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under (5), known e.g. as ABS, MBS, ASA or AES polymers.

7. Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride, and their copolymers such as vinyl chloride/vinylidene chloride, vinyl chloride/vinyl acetate or vinylidene chloride/vinyl acetate copolymers.

8. Polymers which are derived from α,β-unsaturated acids and their derivatives, such as polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkyl acrylate copolymers, acrylonitrile/vinyl chloride copolymers, or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallyl melamine.

11. Homopolymers and copolymers of cyclic ethers such as polyethylene glycols, polyethylene oxide, polypropylene oxide or their copolymers with bis-glycidyl ethers.

12. Polyacetals such as polyoxymethylene, and also those polyoxymethylenes which contain a comonomer, e.g. ethylene oxide.

13. Polyphenylene oxides and sulfides.

14. Polyurethanes which are derived on the one hand from polyethers, polyesters and polybutadienes containing hydroxy end groups, and from aliphatic or aromatic polyisocyanates on the other, as well as their precursors (polyisocyanates, polyols, prepolymers).

15. Polyamides and copolyamides which are derived from diamines and dicarboxylic acids and/or from aminocarboxylic acids or the corresponding lactams, such as polyamide 4, polyamide 6, polyamide 66, polyamide 610, polyamide 11, polyamide 12, poly-2,4,4-trimethylhexamethyleneterephthalamide, poly-m-phenylene-isophthalamide, and their copolymers with polyethers, e.g. with polyethylene glycol, polypropylene glycol or polytetramethylene glycol.

16. Polyureas, polyimides and polyamide imides.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylolcyclohexane terephthalate, and also block polyether esters which are derived from polyethers having hydroxyl end groups and dicarboxylic acids.

18. Polycarbonates.

19. Polysulfones and polyether sulfones.

20. Crosslinked polymers which are derived from aldehydes on the one hand and from phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also their halogen-containing modifications of low combustibility.

23. Crosslinkable acrylic resins which are derived from substituted acrylic esters, e.g. from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, e.g. bis-glycidyl ethers, or from cycloaliphatic diepoxides.

26. Naturally occurring polymers, such as cellulose, rubber and gelatin, and also chemically modified homologous derivatives thereof, such as cellulose acetates, cellulose propionates and cellulose butyrates, and cellulose ethers such as methylcellulose.

27. Natural and synthetic organic substances which constitute pure monomers or mixtures thereof, e.g. mineral oils, animal and vegetable fats, oils and waxes, or oils, waxes and fats derived from synthetic esters (e.g. phthalates, adipates, phosphates or trimellitates), as well as those mixtures of synthetic esters with mineral oils in any weight ratios which are used e.g. as plasticisers for plastics or as spinning preparations, and also aqueous emulsions thereof.

28. Aqueous emulsions of natural or synthetic rubbers, e.g. natural rubber/latex or latices of carboxylated styrene/butadiene copolymers.

The compounds of formula I are particularly effective for stabilising styrene polymers and elastomers.

The stabilised polymers have excellent colour properties and the compatibility of the stabilisers with the polymers is excellent. The compounds of formula I are also very particularly suitable for stabilising lubricants.

The stabilisers are added to the plastics in a concentration of 0.01 to 5% by weight, based on the weight of the material to be stabilised. Preferably, 0.01 to 2.0, most preferably 0.2 to 0.6% by weight of the compounds, based on the weight of the material to be stabilised, are incorporated therein.

The incorporation can be effected after the polymerisation, for example by blending the compounds and, if desired, further additives, into the melt by the methods conventionally employed in the art, before or during forming, or also by applying the dissolved or dispersed compounds to the polymers, if desired with subsequent evaporation of the solvent.

Accordingly, the invention also relates to the plastics stabilised by the addition of 0.01 to 5% by weight of a compound of the formula I and which can, if desired, also contain other known and conventional additives. The stabilised plastics can be used in a very wide variety of forms, for example as sheets, filaments, ribbons, profiles or as binders for lacquers, adhesives or cements.

Examples of further additives with which the stabilisers of the invention can be used, are:

1. Antioxidants 1.1. Alkylated monophenols 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-i-butylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-tert-butyl-4-methoxymethylphenol, 2,6-diphenyl-4-octadecyloxyphenol.

1.2. Alkylated hydroquinones 2,6-di-tert-butyl-4-methoxyphenol, 2,5-di-tert-butyl-hydroquinone or 2,5-di-tert-amyl-hydroquinone.

1.3. Hydroxylated thiophenyl ethers 2,2'-thio-bis-(6-tert-butyl-4-methylphenol), 2,2'-thio-bis-(4-octylphenol), 4,4'-thio-bis-(6-tert-butyl-3-methylphenol) or 4,4'-thio-bis-(6-tert-butyl-2-methylphenol).

1.4. Alkylidene-bisphenols 2,2'-methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], di-(3-tert-butyl-4-hydroxy-5-methylphenyl)-dicyclopentadiene or di-[2-(3'-tert-butyl-2'-hydroxy-5'-methyl-benzyl)-6-tert-butyl-4-methyl-phenyl]terephthalate.

1.5. Benzyl compounds 1,3,5-tri-(3,5-di-tert-butyl-4-hydroxybenzyl)-2,4,6-trimethylbenzene, di-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)-dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxyphenyl-phosphonate or the calcium salt of monoethyl 3,5-di-tert-butyl-4-hydroxybenzyl-phosphonate.

1.6. Acylaminophenols 4-hydroxy-lauric acid anilide, 4-hydroxy-stearic acid anilide or 2,4-bis-octylmercapto-6-(3,5-di-tert-butyl-4-hydroxyanilino)-S-triazine.

1.7. Esters of β-(3,5-di-tert-butyl-4-hydroxyphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, trishydroxyethyl isocyanurate or dihydroxyethyloxalamide.

1.8. Esters of β-(5-tert-butyl-4-hydroxy-3-methylphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-hydroxyethyl isocyanurate or dihydroxyethyloxalamide.

1.9. Amides of β-(3,5-di-tert-butyl-4-hydroxyphenyl)-propionic acid, for example N,N'-di-(3,5-di-tert-butyl-4-hydroxyphenylpropionyl)hexamethylenediamine, N,N'-di-(3,5-di-tert-butyl-4-hydroxyphenylpropionyl)-trimethylenediamine or N,N'-di-(3,5-di-tert-butyl-4-hydroxyphenylpropionyl)hydrazine.

2. UV-absorbers and light stabilisers

2.1. 2-(2'-Hydroxyphenyl)-benztriazoles, for example 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec.-butyl-5'-tert-butyl-, 4'-octoxy-, 3',5'-di-tert-amyl-, 3',5'-di-(1,1,3,3-tetramethylbutyl)- and 3',5'-di-(α,α-dimethylbenzyl)-2-(2'-hydroxyphenyl)-benztriazole.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy-derivatives.

2.3. Esters of substituted and unsubstituted benzoic acids, for example 4-tert-butyl-phenyl salicylate, phenyl salicylate, octylphenyl salicylate, dibenzoylresorcinol, bis-(4-tert-butylbenzoyl)-resorcinol, benzoylresorcinol and 2,4-di-tert-butyl-phenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxy-cinnamate, methyl α-cyano-β-methyl-p-methoxy-cinnamate, butyl α-cyano-β-methyl-p-methoxy-cinnamate, methyl α-carbomethoxy-p-methoxy-cinnamate and N-(β-carbomethoxy-β-cyanovinyl)-2-methyl-indoline.

2.5. Nickel compounds, for example nickel complexes of 2,2'-thio-bis-[4-(1,1,3,3-tetramethylbutyl)phenol], such as the 1:1 complex or the 1:2 complex, with or without additional ligands such as n-butylamine, triethanolamine or N-cyclohexyl-diethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketone oxime and nickel complexes of 1-phenyl-4-lauroyl-5-hydroxy-pyrazole, with or without additional ligands.

2.6. Sterically hindered amines, for example bis-(2,2,6,6-tetramethylpiperidyl)sebacate, bis-(1,2,2,6,6-pentamethylpiperidyl)sebacate, bis-(1,2,2,6,6-pentamethylpiperidyl)n-butyl-3,5-di-tert-butyl-4-hydroxybenzyl-malonate, the condensation product of 1-hydroxyethyl-2,2,6,6-tetramethyl-4-hydroxypiperidine and succinic acid, the condensation product of N,N'-(2,2,6,6-tetramethylpiperidyl)-hexamethylenediamine and 4-tert-octylamino-2,6-dichloro-1,3,5-s-triazine, and tris-(2,2,6,6-tetramethylpiperidyl)nitrilotriacetate.

2.7. Oxalic acid diamides, for example 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyl-oxanilide, mixtures of ortho- and paramethoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole and bis-benzylidene-oxalic acid dihydrazide.

4. Phosphites and phosphonites, for example triphenyl phosphite, diphenyl alkyl phosphites, phenyl dialkyl phosphites, tri(nonylphenyl)phosphite, trilauryl phosphite, trioctadecyl phosphite, distearyl-pentaerythritol diphosphite, tris-(2,4-di-tert-butylphenyl)-phosphite, diisodecyl-pentaerythritol diphosphite, di-(2,4-di-tert-butylphenyl)-pentaerythritol diphosphite, tristearylsorbitol triphosphite and tetrakis-(2,4-di-tert-butylphenyl)-4,4'-biphenylene diphosphonite.

5. Compounds which decompose peroxide, for example esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatechoate or tin pyrocatechoate.

8. Nucleating agents, for example 4-tert-butylbenzoic acid, adipic acid and diphenylacetic acid.

9. Fillers and reinforcing agents, for example calcium carbonates, silicates, glass fibres, asbestos, talc, kaolin, mica, barium sulfate, metal oxides and metal hydroxides, carbon black and graphite.

10. Other additives, for example plasticisers, lubricants, emulsifiers, pigments, fluorescent whitening agents, flameproofing agents, antistatic agents and blowing agents.

EXAMPLE 1

3,5-di-(3',5'-di-tert-butyl-4-hydroxybenzyl)-2,4-dimethyl-6-tert-butylphenol 21.5 g of 2,4-dimethyl-6-tert-butylphenol are dissolved in 60 ml of methanol and to this solution are added 11 g of 80% sulfuric acid. With stirring and under nitrogen, 60 g of 4-methoxymethyl-2,6-di-tert-butylphenol are then added at about 70° C. (reflux) over 6 hours. The reaction mixture is kept for a further 6 hours at 70° C. Upon cooling, colourless crystals of the reaction product precipitate. The crystals are filtered with suction and purified by digestion with hexane, filtration, digestion with water containing NaOH, and further filtration. Melting point: 140° C. (recrystallisation from methanol).

EXAMPLE 2

The procedure of Example 1 is repeated, using an aliquot amount of 2,4,6-trimethylphenol instead of 2,4-dimethyl-6-tert-butylphenol, to give 3,5-di-(3',5'-di-tert-butyl-4-hydroxybenzyl)-2,4,6-trimethylphenol with a melting point of 204° C.

EXAMPLE 3

100 parts by weight of unstabilised ABS powder are mixed with a stabiliser as indicated in Tables I and II. The resultant mixture is compounded for 5 minutes at a maximum temperature of 170° C. on a two-roll mill and the rolled sheet obtained is then stripped off. The sheet is then pressed on a hydraulic laboratory press for 6 minutes at 180° C. to 1 mm sheets from which test specimens measuring 50×20 mm are punched out.

The effectiveness of the stabiliser added to the specimens is tested by heat ageing in a forced draught oven at 180° C. Reference value for the damage (oxidation) which has occurred during ageing is the infrared absorption spectrum of the surface, which is obtained by reflection spectroscopy. In particular, the increase in carbonyl extinction (1720 cm$^{-1}$) is monitored as a function of the time and compared with an absorption band which remains constant (1455 cm$^{-1}$). The degradation is measured in accordance with the equation:

$$V = \frac{\text{optical density at 1720 cm}^{-1} (>C=O)}{\text{optical density at 1455 cm}^{-1} (>CH_2)}$$

The time after which V has reached the value 0.1 ($t_{0.1}$) is taken as arbitrary end point.

TABLE I

Test in ABS without synergist.

| Stabiliser of Example 0.25% by weight | | Oven ageing at 180° C. Y.I. ASTM D 1925 after oven ageing (minutes) | | | | | |
|---|---|---|---|---|---|---|---|
| | $t_{0.1}$ | 0 | 30 | 60 | 90 | 120 | 150 |
| 1 | 70' | 13.5 | 26.4 | 30.0 | 55.1 | 69.1 | |
| 2 | 35' | 19.7 | 33 | 48 | 69 | | |
| without stabiliser | 7' | 17 | 53 | 73 | 83 | | |

TABLE II

Test in ABS with the synergist DLTP (dilaurylthiodipropionate).

| Stabiliser of Example + DLTDP 0.25% by weight of stabiliser 0.25% by weight of DLTDP | | Oven ageing at 180° C. Y.I. ASTM after oven ageing (minutes) | | | | | |
|---|---|---|---|---|---|---|---|
| | $t_{0.1}$ | 0 | 30 | 60 | 90 | 120 | 150 |
| 1 | 107' | 15.0 | 21.0 | 27.3 | 29.8 | 59.5 | |
| 2 | 83' | 18.2 | 31 | 37 | 51 | | |
| without stabiliser | 7' | 17 | 53 | 73 | 83 | | |

EXAMPLE 4

Impact-resistant polystyrene containing 8% by weight of polybutadiene (high-cis) and 0.035% by weight of 2,6-di-tert-butyl-p-cresol as basic stabiliser, 0.05% by weight of zinc stearate as lubricant and 0.1% by weight of one of the antioxidants of this invention (each identified in Tables III and IV with the number of the corresponding preparatory Example), is extruded twice at 220° C. and the resultant granulate is pressed to 2 mm test specimens at 185° C. over 3 minutes.

These test specimens are subjected to oven ageing in a forced draught oven and the following properties are determined:

(a) The Yellowness Index (YI) according to ASTM D 1925 is measured at 80° C. (measurement after 0, 250, 500, 750 and 1000 hours) and at 160° C. (measurement after 0, 60, 90, 120 and 180 minutes). The results are reported in Table III.

(b) The impact strength (IS) in kp.cm/cm$^2$ is determined after ageing at 160° C. (measurement after 30, 60, 120, 150, 180, 240, 300, 360, 420 and 480 minutes). The results are reported in Table IV.

TABLE III

| Stabiliser of Example | Y.I. at 80° C. (hours) | | | | | Y.I. at 160° C. (minutes) | | | | |
|---|---|---|---|---|---|---|---|---|---|---|
| | 0 | 250 | 500 | 750 | 1000 | 0 | 60 | 90 | 120 | 180 |
| without stabiliser | 0.5 | 18 | 24 | 36 | 48 | 0 | 17 | 37 | 47 | 73 |
| 1 | 0.8 | 15 | 22 | 29 | 37 | 1 | 17 | 22 | 29 | 36 |

TABLE IV

| Stabiliser of Example | IS after ageing at 160° C. (minutes) | | | | | | | | | |
|---|---|---|---|---|---|---|---|---|---|---|
| | 30 | 60 | 120 | 150 | 180 | 240 | 300 | 360 | 420 | 480 |
| without stabiliser | 10.4 | | | | | | | | | |

TABLE IV-continued

| Stabiliser of Example | IS after ageing at 160° C. (minutes) | | | | | | | | |
|---|---|---|---|---|---|---|---|---|---|
| | 30 | 60 | 120 | 150 | 180 | 240 | 300 | 360 | 420 | 480 |
| 1 | X | X | X | X | X | X | X | X | 7.9 | |

X = specimen not broken.

What is claimed is:

1. A compound of formula I

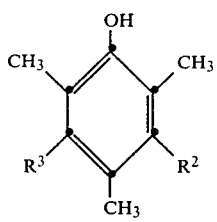

wherein
$R^1$ and $R^4$ are methyl,
$R^2$ and $R^3$ are each a radical of formula II

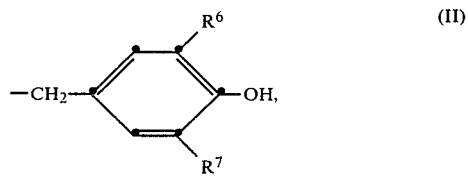

wherein $R^6$ is $C_1$–$C_{12}$ alkyl, $C_5$–$C_8$ cycloalkyl, $C_6$–$C_{10}$ aryl, $C_7$–$C_{10}$ aralkyl or $C_7$–$C_{10}$ alkaryl and $R^7$ is $C_4$–$C_{12}$ alkyl, $C_5$–$C_8$ cycloalkyl, $C_6$–$C_{10}$ aryl, $C_7$–$C_{10}$ aralkyl or $C_7$–$C_{10}$ alkaryl.

2. A compound according to claim 1 wherein $R^6$ and $R^7$ are each tert-butyl.

3. The compound according to claim 1 which is 3,5-di-(3,5-di-tert-butyl-4-hydroxybenzyl)-2,4,6-trimethylphenol.

4. A lubricating oil stabilized with an effective amount of a compound according to claim 1.

5. A stabilized polymer composition which comprises
    (a) a graft polymer based on acrylonitrile, butadiene and styrene or impact-resistant polystyrene, and
    (b) an effective amount of a compound according to claim 1.

* * * * *